United States Patent [19]

Meek et al.

[11] Plant 4,973

[45] Jan. 11, 1983

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 272,330

[22] Filed: Jun. 10, 1981

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant known by the cultivar name Echo and particularly characterized as to uniqueness by the combined characteristics of flat capitulum form, spooned anemone capitulum type; ivory white ray floret color; diameter across face of capitulum ranging from 70 to 75 mm. at maturity; uniform nine week photo-periodic flowering response to short days; medium plant height when grown as a pinched spray pot, and upright branching pattern.

3 Drawing Figures

The present invention comprises a new and distinct cultivar of *Chrysanthemum morifolium,* Ramat., hereinafter referred to by the cultivar name Echo.

Echo is a product of a planned breeding program which had the objective of creating new chrysanthemum cultivars for pinched spray pot mum programs having spooned anemone capitulum type, white or yellow ray floret color, nine week flowering response and having the ability to produce commercially acceptable quality in year-round programs. Such traits in combination were not present in previously available commercial cultivars.

Echo was originated from a cross made in a controlled breeding program in Salinas, Calif. in 1977. The female parent was an unnamed white single spoon originated by the present inventors from a hybridization of two unnamed seedlings. The male parent of Echo was an unnamed yellow anemone spoon originated from a cross between Smile (unpatented, commercially available) and Spindles (unpatented; commercially available).

Echo was discovered and selected as one flowering plant within the progeny of the stated cross by William E. Duffett on Nov. 9, 1978 in a controlled environment in Salinas, Calif.

The first act of asexual reproduction of Echo was accomplished when vegetative cuttings were taken from the initial selection in February, 1979 in a controlled environment in Salinas, Calif. by a technician working under formulations established and supervised by Jack M. Meek. Horticultural examination of selected units initiated Aug. 22, 1979 has demonstrated that the combination of characteristics as herein disclosed for Echo are firmly fixed and are retained through successive generations of asexual reproduction.

Echo has not been observed under all possible environmental conditions. The phenotype may vary significantly with variations in environment such as temperature, light intensity and day length. The observations, measurements and comparisons describe plants grown in Salinas, Calif. under greenhouse conditions which approximate those generally used in commercial practice.

The following traits have been repeatedly observed and are determined to be basic characteristics of Echo which in combination distinguish this chrysanthemum as a new and distinct cultivar:

(1) flat capitulum form;

(2) spooned anemone capitulum type;

(3) ivory white ray floret color;

(4) diameter across face of capitulum ranging from 70 to 75 mm. at maturity;

(5) uniform nine week photoperiodic flowering response to short days;

(6) medium plant height (requiring 1–2 long day weeks prior to pinch and short days, and one application 2500 ppm B-9 SP 14 to 21 days after the beginning of short days to attain a flowered plant height of 25 to 35 cm.); and (7) upright branching pattern.

The accompanying photographic drawings illustrate typical foliage and inflorescence characteristics of Echo. Sheet 1 is a color photograph of a plant of Echo grown as a spray pot, with the colors being as accurate as possible with renditions of this type. Sheet 2 is a black and white photograph of three views of the inflorescence of Echo. Sheet 3 shows the foliate of Echo in three stages of growth.

Of the many commercial cultivars known to the present inventors, the most similar in comparison to Echo is Quills, disclosed in U.S. Plant Pat. No. 4,401. Reference is made to attached Chart A which compares certain characteristics of Echo to those same characteristics of Quills. General comparisons are as follows:

(1) In comparison to Quills, Echo has more ivory ray floret color, anemone capitulum type, smaller diameter across face of capitulum and longer flowering response period. The capitulum form, ray floret shape, branching pattern and plant height of Echo are similar to those same characteristics of Quills.

In the following description, color references are made to The Royal Horticultural Society Colour Chart. The color values were determined between 8:00 and 8:30 A.M. on Oct. 6, 1980 under 150 foot-candle light intensity at Salinas, Calif.

CLASSIFICATION

Botanical: *Chrysanthemum morifolium,* Ramat., cv Echo.

Commercial: Pinched spray spooned anemone pot mum.

I. INFLORESCENCE

A. Capitulum:

*Form.*—Flat.

*Type.*—Spooned anemone, two to three rows of spooned ray florets surrounding elongated, anemone disc florets.

*Diameter across face.*—70 to 75 mm.

B. Corolla of ray florets:

*Color (general tonality from a distance of three meters).*—Ivory white, 155 D.

*Color (abaxial).*—4-D oxidizing to 155-D.

*Color (adaxial).*—155-D.

*Shape.*—Tubular, flaring at tip to give irregular spooned appearance.

C. Corolla of disc florets:

*Color (mature).*—155-A.

*Color (immature).*—Approximately 143-A to 5-A.

*Shape.*—Tubular, flaring at tip to give irregular spooned appearance.

D. Reproductive organs:

*Androecium.*—Present in disc florets only; moderate pollen.

*Gynoecium.*—Present in both ray and disc florets.

II. PLANT

A. General appearance:

*Height.*—Medium; 25 to 35 cm. given 2 long day weeks before pinch and lights out, and 1–2 applications 2500 B-9 SP after lights out.

*Branching pattern.*—Free breaking with upright angle from main stem.

B. Foliage:

*Color (abaxial).*—147-A.

*Color (adaxial).*—147-B.

*Shape.*—Moderately lobed and serrated.

CHART A

COMPARISON OF ECHO AND QUILLS

| CULTIVAR | RAY FLORET COLOR | CAPITULUM FORM AND TYPE | BRANCHING PATTERN |
|---|---|---|---|
| ECHO | Ivory White | Flat Anemone Spoon | Upright |
| QUILLS | White | Flat Spooned Daisy | Upright |

| CULTIVAR | DIAMETER ACROSS FACE OF CAPITULUM | PLANT HEIGHT | FLOWERING RESPONSE PERIOD |
|---|---|---|---|
| ECHO | 70 to 75 mm. | Medium 25 to 35 cm. | 9 week |
| QUILLS | 65 to 100 mm. | Medium 25 to 35 cm. | 7 Week |

COMPARISONS MADE OF PLANTS GROWN AS PINCHED SPRAY POTS IN SALINAS, CALIFORNIA.

We claim:

1. A new and distinct cultivar of *Chrysanthemum morifolium,* Ramat., plant known by the cultivar name of Echo, as described and illustrated, and particularly characterized as to uniqueness by the combined characteristics of flat capitulum form; spooned anemone capitulum type; ivory white ray floret color; diameter across face of capitulum ranging from 70 to 75 mm. at maturity; uniform nine week flowering response; medium plant height, and upright branching pattern.

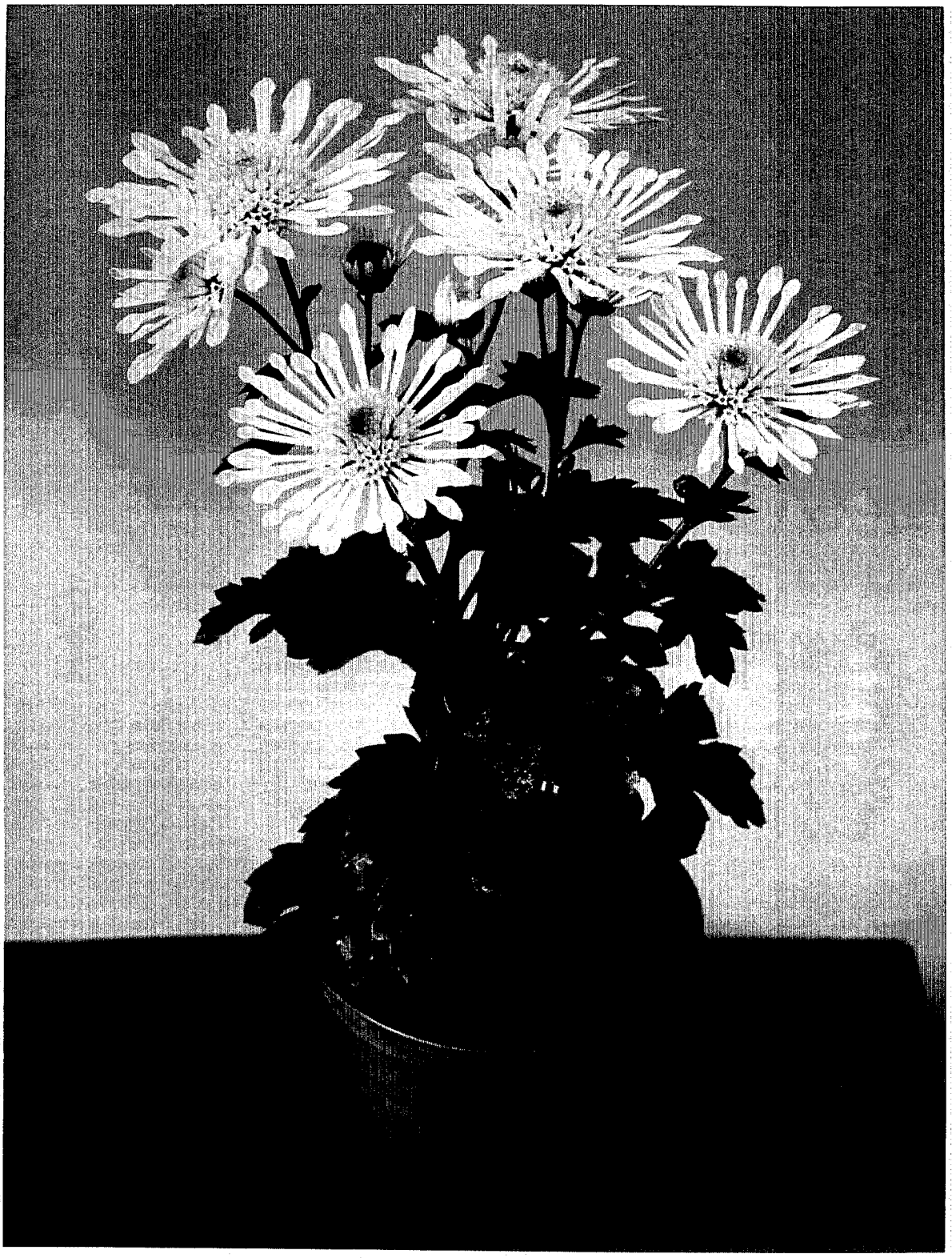

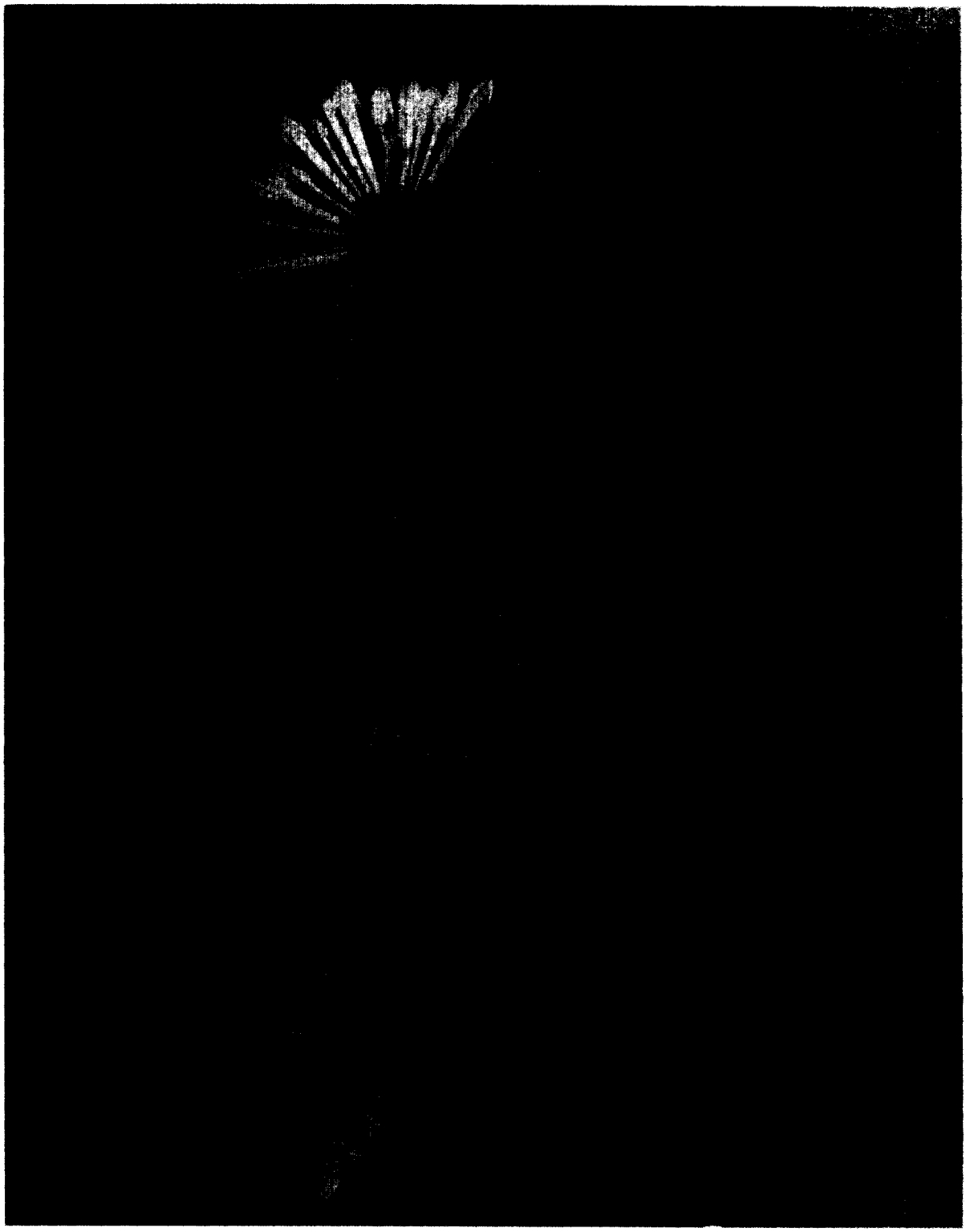

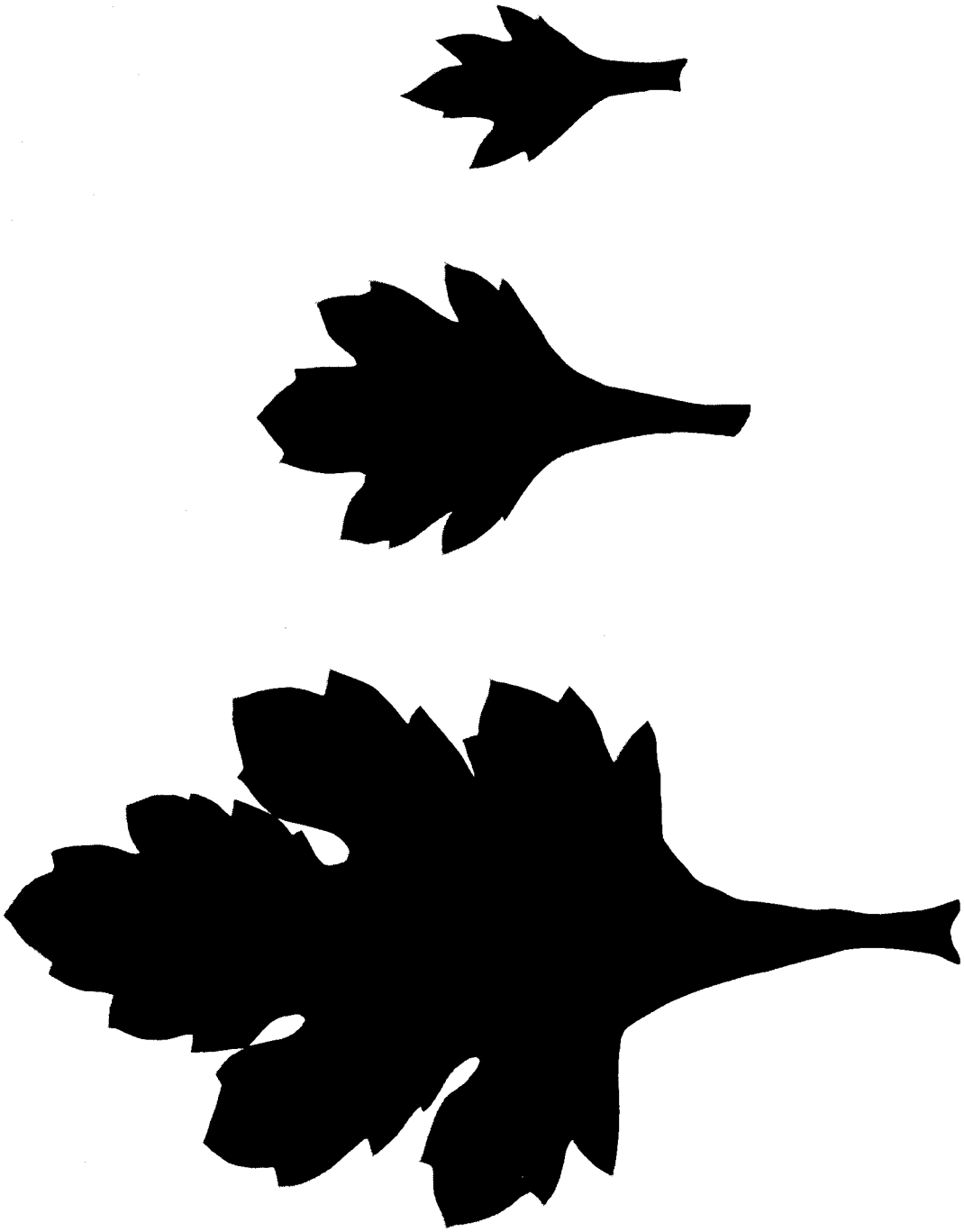

* * * * *